United States Patent [19]

Matura et al.

[11] Patent Number: 5,327,890
[45] Date of Patent: Jul. 12, 1994

[54] APPARATUS FOR TREATING A PATIENT WITH ACOUSTIC WAVES

[75] Inventors: Eike Matura, Erlangen; Hans-Christian Bock, Uttenreuth, both of Fed. Rep. of Germany

[73] Assignee: Siemens Aktiengesellschaft, Munich

[21] Appl. No.: 941,887

[22] Filed: Sep. 8, 1992

[30] Foreign Application Priority Data

Sep. 16, 1991 [DE] Fed. Rep. of Germany ....... 4130761

[51] Int. Cl.$^5$ .................. A61B 6/00; A61B 17/22
[52] U.S. Cl. ................... 128/653.1; 601/2; 601/4
[58] Field of Search ........ 128/24 AA, 24 EL, 660.03, 128/653.1

[56] References Cited

U.S. PATENT DOCUMENTS

| 4,669,483 | 6/1987 | Hepp et al. . |
| 4,674,505 | 6/1987 | Pauli et al. . |
| 4,979,501 | 12/1990 | Valchanov et al. . |
| 5,044,354 | 9/1991 | Goldhorn et al. . |
| 5,060,650 | 10/1991 | Wurster et al. . |
| 5,065,741 | 11/1991 | Uchiyama et al. ............. 128/24 EL |
| 5,230,329 | 7/1993 | Puppo ............................ 128/24 EL |

FOREIGN PATENT DOCUMENTS

| 0169311 | 1/1986 | European Pat. Off. . |
| 0277489 | 8/1988 | European Pat. Off. . |
| 3312014 | 11/1985 | Fed. Rep. of Germany . |
| 3835317 | 4/1990 | Fed. Rep. of Germany . |
| 3840077 | 5/1990 | Fed. Rep. of Germany . |
| 4021102 | 1/1991 | Fed. Rep. of Germany . |
| 4033439 | 11/1991 | Fed. Rep. of Germany . |
| 2120060 | 11/1983 | United Kingdom . |

Primary Examiner—Ruth S. Smith
Attorney, Agent, or Firm—Hill, Steadman & Simpson

[57] ABSTRACT

An apparatus for treating a patient with acoustic waves has a source of acoustic waves and an X-ray locating system, which includes an X-ray radiator and a radiation detector, which are mounted opposite each other on a C-arm. The C-arm is adjustable along its outer circumference around its central axis. The source of acoustic waves is adjustable along the inner circumference of the C-arm such that the acoustic axis of the acoustic wave source constantly intersects the central axis of the C-arm.

7 Claims, 1 Drawing Sheet

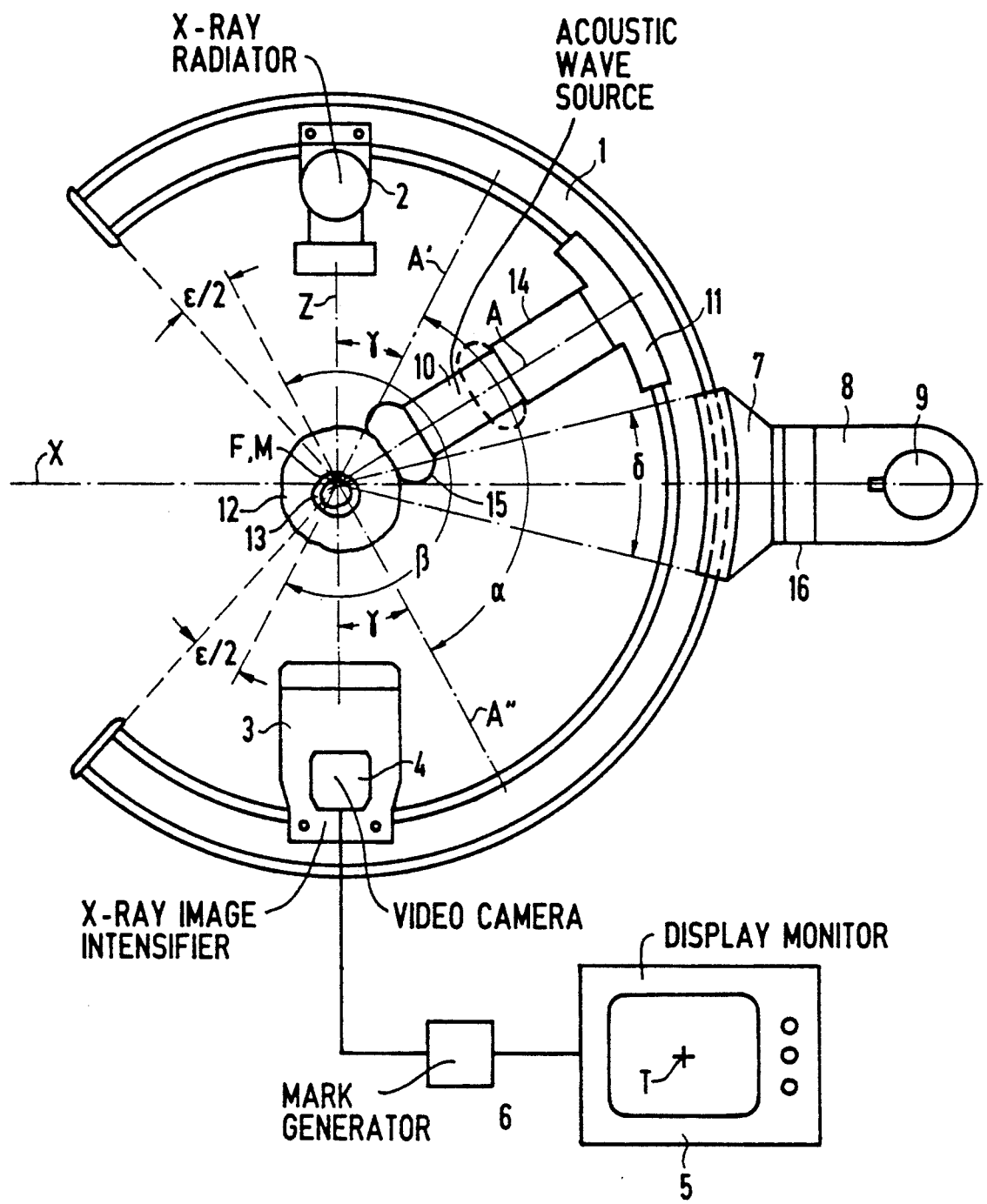

APPARATUS FOR TREATING A PATIENT WITH ACOUSTIC WAVES

BACKGROUND OF THE INVENTION

1. Field of the Invention

The present invention relates to an apparatus for treating a patient with acoustic waves, of the type including a source of acoustic waves and an X-ray locating system, having an X-ray radiator and a radiation detector which are mounted opposite each other on a C-arm, the C-arm being rotatable around its central axis in a holder.

2. Description of the Prior Art

Treatment systems for generating acoustic waves in the form of pressure pulses, such as shock waves, are used for lithotripsy and for the treatment of pathological tissue conditions. It is known from U.S. Pat. No. 4,979,501 to employ acoustic waves in the treatment of bone pathologies. In this known system, an X-ray locating system is provided which includes an X-ray radiator and a radiation detector mounted on a C-arm. The C-arm is mounted on a carrier, together with the source of acoustic waves, the carrier being rectilinearly adjustable. The C-arm can be rotated around its circumference through an angle of ±30°. This adjustability range is sufficient to meet the needs for locating purposes, to permit a body part to be treated, for example an extremity, to be radiated with X-rays at different angles. The capability of adjusting the source of acoustic waves only rectilinearly, however, presents disadvantages in the treatment of bone pathologies in the region of the extremities, because the patient or the extremity to be treated has to be shifted frequently during treatment in order to assure that a position is always maintained relative to the acoustic wave source which permits the acoustic waves to pass unimpeded to the treatment zone. The necessity of such frequent shifting is uncomfortable for the patient, who under some circumstances suffers pain in the process, and is also bothersome to the medical personnel because of the physical exertions associated with such shifting.

SUMMARY OF THE INVENTION

It is an object of the present invention to provide an apparatus for the treatment of a patient with acoustic waves, which employs an X-ray locating system mounted on a C-arm, which insures that the acoustic waves will pass from the acoustic wave source to the treatment zone unimpeded without the necessity of shifting the patient or the extremity to be treated.

The above object is achieved in accordance with the principals with the present invention in an apparatus having an X-ray locating system with an X-ray radiator and a X-ray detector mounted on a C-arm, which is rotatable around its central axis, and wherein the source of acoustic waves is mounted on the inner circumference of the C-arm such that the acoustic axis of the acoustic wave source always intersects the central axis of the C-arm. Because the acoustic wave source is adjustable around the inner circumference of the C-arm, it is possible in a large number of cases to align the acoustic wave source and the body of the patient, or the extremity, to be treated relative to each other in a manner which does not require shifting of the patient during treatment.

In accordance with the principals of the present invention, it is also possible to adjust the path of the acoustic waves independently of the X-ray locating system, or simultaneously with the locating system. Because the acoustic axis of the acoustic wave source always intersects the central axis of the C-arm, a defined spacial relationship between the acoustic wave source and the X-ray locating system is known.

In a further embodiment of the invention, the sum of the angle through which the C-arm is rotatable around its outer circumference in its holder, and the angle through which the acoustic wave source is adjustable around the inner circumference of the C-arm, is equal to at least 360°. This permits the acoustic wave source to be moved through a complete circular path around the patient or the extremity to be treated. Arbitrary angular positions of the patient or of the extremity and the propagation path of the acoustic waves relative to each other, with respect to the central axis of the C-arm, are thus possible without the necessity of repositioning the patient or the extremity.

If the acoustic wave source is of the type which deliver focussed acoustic waves, in a further embodiment of the invention the focus zone of the acoustic waves, at least during the time of treatment, lies on the central axis of the C-arm. This insures a defined position of the focus zone relative to the X-ray locating system. In order to provide more space to accommodate placement of the patient in or removal of the patient from the overall apparatus before and after the actual treatment, the acoustic wave source can be moveable along the direction of its acoustic axis, so as to be adjustable toward and away from the central axis of the C-arm.

In order to permit adaption of the position of the X-ray radiator and the X-ray detector (X-ray image intensifier) of the X-ray locating system to individual treatment requirements, the C-arm can be made pivotable through ±180° around a further axis which intersects the central axis of the C-arm, preferably at a right angle, and preferably at the same point as the central ray of the X-ray locating system intersects the central axis of the C-arm. It is thus possible to exchange the respective positions of the X-ray radiator and the radiation detector relative to the patient.

DESCRIPTION OF THE DRAWING

The single FIGURE is a side elevational view of an apparatus for the treatment of a patient with acoustic waves constructed in accordance with the principals of the present invention, in the exemplary embodiment of an apparatus for treating bone pathologies, with certain electronic components being shown in block diagram form.

DESCRIPTION OF THE PREFERRED EMBODIMENTS

As shown in the drawing, the apparatus constructed in accordance with the principals of the present invention has a circularly curved C-arm 1, on which an X-ray radiator 2 and a radiation detector, in the form of an X-ray image intensifier 3, are disposed opposite each other. The X-ray radiator 2 generates an X-ray beam having a central ray Z, which intersects the central axis M of the C-arm 1 and is centrally incident on the input luminescence screen of the X-ray image intensifier 3. The image at the output luminescence screen of the X-ray image intensifier 3 is received by a video camera 4, integrated within the X-ray image intensifier 3, and this image is converted into a video image on a known manner which is displayed on a monitor 5. A mark generator 6 is connected between the video camera 4 and the monitor 5, which mixes a mark T into the X-ray image represented on the screen on the monitor 5. The position of the mark T within the image corresponds to the intersection point of the central ray Z with the input luminescence screen of the X-ray image intensifier 3. The X-ray source 2 is supplied with the necessary operating voltages from a high voltage supply (not shown) in a known manner.

The C-arm 1 has a double T-shaped cross section. Its outer flange is received in a holder 7 such that the C-arm 1 can be rotated around its outer circumference around its central axis M. Such rotation can be accomplished in a known manner, either manually or by motor. The holder 7 is mounted on a carrying arm 8 which is disposed so as to be slidable along the longitudinal axis of a guide rod 9 but, due to a keyed engagement with the guide rod 9, the carrying arm 8 is not rotatable around the guide rod 9. The guide rod 9 is mounted a fixed base (not shown), and the sliding of the carrying arm 8 along the guide rod 9 can be undertaken manually or by motor, in a known manner.

The apparatus also includes a source of focused acoustic waves, in the form of a pressure pulse or shock wave source 10 (a pressure pulse being an incipient shock wave). The shock wave source 10 in the apparatus of the invention is preferably an electromagnetic shock wave source of the type described, for example, in U.S. Pat. No. 4,674,505 or in German OS 33 12 014. The shock wave source 10 has a focus zone F in which the generated shock waves converge, and which lies on the acoustic axis A of the shock wave source 10. The shock wave source 10 is mounted on a carriage 11 which is guided on the inner flange of the C-arm 1 so as to be moveable around the inner circumference of the C-arm 1. In accordance with the principals of the present invention, such movement takes place so that the acoustic axis A of the shock wave source 10, regardless of the position of the carriage 11 on the C-arm 1, intersects the central axis M of the C-arm 1 at the same point as does the central ray Z of the X-ray beam. Furthermore, during treatment of a patient or of a body part with acoustic waves, the central axis M of the C-arm 1 proceeds through the center of the focus zone F, regardless of the position of the carriage 11 on the C-arm 1. The adjustment of the shock wave source 10 and the carriage 11 around the inner circumference of the C-arm 1 occurs between two end positions, bounded by the X-ray radiator 2 and the X-ray image intensifier 3. The respective positions of the acoustic axis of the shock wave source 10 when the shock wave source 10 is at those extreme positions are shown in the drawing reference to A' and to A''. Movement of the carriage 11 and the shock wave source 10 around the inner circumference of the C-arm 1 can take place manually or by motor. The shock wave source 10 is therefore adjustable around the circumference of the C-arm 1 through a total angle $\alpha$. The C-arm 1 extends through an angle of more than 180°, which permits the C-arm 1 to be rotated at its outer circumference in the holder 7 through an angle $\beta$, which corresponds at least to the difference $360° - \alpha$. By rotating the C-arm 1 around its outer circumference in the holder 7, and adjusting the shock wave source 10 and its carriage 11 along the inner circumference of the C-arm 1, it is thus possible to conduct the shock wave source 10 through a complete circular path around the central axis M. This is advantageous, as described below, particularly in the treatment of bone diseases in the region of the extremities. To achieve this capability, the C-arm 1 must extend beyond the angle $\beta$ at least by a length defined by the angle $\delta$ subtended by the holder 7. In the embodiment shown in the drawing, this is accomplished by extending each end of the C-arm 1 through an additional angle $\epsilon/2$ ($\epsilon \geq \delta$).

If a bone pathology is to be treated in the region of an extremity, for example a fracture of an upper arm 12, the patient is placed on a support table (not shown) such that the central axis of the upper arm bone approximately coincides with the central axis M of the C-arm 1, when the upper arm is spread at an angle of 90° from the body of the patient. The upper arm 12, and the upper arm bone 13, are schematically indicated in cross section in the drawing. The upper arm 12 is then fixed in the aforementioned position by known orthopedic measures. The positioning should take place such that the upper arm 12 is freely accessible over the entire extent in the region of the fracture. The X-ray locating system is then activated and the carrying arm 8 is shifted along the guide rod 9 so that the fracture is located approximately in the center of the X-ray image which is visible on the monitor 5. By careful shifting of the upper arm 12 in a direction extending transversely both to the central axis M of the C-arm 1 and to the central ray Z of the X-ray beam of the X-ray locating system, and possibly by further shifting the carrying arm 8 along the guide rod 9, the upper arm 12 and the C-arm 1 are aligned relative to each other such that the mark T coincides with the zone of the fracture that is to be treated with acoustic waves. When this has been achieved, the C-arm 1 is pivoted through a defined angle $\gamma$ (preferably $\gamma = 0.5 \times 180° - \alpha$), and the upper arm 12, if necessary, is carefully shifted in a direction corresponding to the direction of the central ray Z before pivoting the C-arm 1 through the angle $\gamma$, until the mark T again coincides with the zone which is to be treated with acoustic waves.

The zone to be treated with acoustic waves is now located at the intersection of the central axis M of the C-arm 1 and the central ray Z and the acoustic axis A. The shock wave source 10 can be telescopically adjusted by a tubular guide 14 which is connected to the carriage 11, so that the shock wave source 10 can be moved toward and away from the treatment site of the apparatus, the intersection point of the central axis M and the acoustic axis A being the center of the treatment site. Prior to beginning the treatment, the guide 14 is retracted so that the application end of the shock wave source 10 is in the standby position indicated by dash lines in the drawing. This provides more room for the initial patient positioning. The shock wave source 10 is then brought to its working position, shown in solid lines in the drawing, by extending the guide 14. The guide 14 can be operated either manually or by motor.

When the shock wave source 10 is in its working position, the focus zone F of the acoustic waves occupies the desired position at the intersection point of the acoustic axis A and the central axis M of the C-arm 1 and the central ray Z. The shock wave source 10 is positioned relative to the body part to be treated so that a compressible coupling cushion 15 of the shock wave source 10, which serves to acoustically couple the acoustic waves into the body part, is pressed against the surface of the upper arm 12. The carriage 11 was moved along the circumference of the C-arm 1 through an angle selected dependent upon the region to be treated by acoustic waves to cause the acoustic axis A of the shock wave source 10 to be oriented as described above.

Because the C-arm 1 is adjustable around its outer circumference in the holder 7 independently of the adjustment of the carriage 11 and the shock wave 10 around the inner circumference of the C-arm 1, it is possible, after completely the coupling of the shock wave source 10 to the upper arm 12, to check whether the upper arm bone 13 is still aligned in the requisite manner relative to the focus zone F of the shock wave source 10. This is undertaken in a procedure wherein, first, by determining, using the X-ray locating system, the position which the C-arm 1 occupies relative to the shock wave source 10 after the shock wave source 10 has been coupled to the upper arm 12. While retaining the shock wave source in its position relative to the upper arm 12, the C-arm 1 is moved through the angle γ to its initial position, whereupon another check of the position of the region of the fracture to be treated relative to the focus zone F is undertaken. If, during coupling of the shock wave source 10, displacements have occurred, despite the efforts to fix the position of the upper arm 12, such displacements can be corrected at this time. In the rotation of the C-arm 1 through the angle γ, a relative movement occurs between the carriage 11 and the C-arm 1, in order to assure that the shock wave source 10 remains in its designated spacial position. If the C-arm 1 and the holder 7 and the carriage 11 are adjustable by respective motors, the C-arm 1 can easily be rotated while simultaneously retaining the desired spacial alignment of the shock wave source 10, with the respective drive motors being driven such that the C-arm 1 in the holder 7 and the carriage 11 on the C-arm 1 are moved with equal but opposite angular velocity.

When it has been made certain that the zone to be treated is present in the required manner within the focus zone F of the shock wave source 10, the region of the upper arm bone 13 which is contained in the focus zone F of the acoustic waves is subjected to a series of such acoustic waves, thereby producing a stimulation of the bone growth. If further portions of the fracture are to be subjected to acoustic waves, this is undertaken in a procedure in which each location to be treated is brought into the intersection of the central axis M of the C-arm 1 with the central ray Z and the acoustic axis A in the manner described above, and the shock wave source 10 is moved for coupling to the upper arm 12 into a position so that its acoustic axis A is oriented at the desired angle relative to the upper arm bone 12. Because, as already explained, the shock wave source 10 can be moved through a complete circular path around the central axis M of the C-arm 1, any desired angular positions can be achieved.

For some treatments, it can be useful if the X-ray radiator and the X-ray image intensifier 3 can exchange their positions relative to those shown in FIG. 1, so that the X-ray radiator 2 can be positioned below the treatment site and the X-ray image intensifier 3 can be positioned above the treatment site. This can be achieved by providing the carrying arm 8 with a rotating joint 16 which, either by motor or manually, permits the C-arm 1 to be rotated around an axis X extending perpendicularly to the central axis M, and intersecting the axis M at the same point as the central beam Z and the acoustic axis A. The rotatable joint 16 permits the C-arm 1 to be rotated around the axis X through ±180°.

For treatments other than in the example described above, the intersection of the acoustic axis A with the central axis M need not necessarily coincide with the intersection of the central ray Z with the central axis M. Any offset between these respective points of intersection can be corrected by making a corresponding correction (offset) in the position of the mark T.

As noted at the outset, the invention has been described in the above context of an apparatus for the treatment of bone pathologies, however, it will be understood that the inventive concept disclosed herein can be used for many other types of medical therapies, as well as for non-medical uses.

Moreover, the source of acoustic waves does not necessarily have to be a shock wave source, as described in the above example. Alternatively, a pressure pulse source which emits tractive pulses (i.e., so called "negative pressure" pulses) or a therapeutic ultrasound source may be used. The use of such sources of acoustic waves is beneficial, for example, in the treatment of tumors.

Although other modifications and changes may be suggested by those skilled in the art, it is the intention of the inventors to embody within the patent awarded hereon all changes and modifications are reasonably and properly come within the scope of their contribution to the art.

We claim as our invention:

1. An apparatus for treating a patient with acoustic waves comprising:
    an X-ray locating system including a C-arm partially surrounding a treatment site and an X-ray source and a radiation detector mounted on said C-arm on opposite sides of said treatment site, and C-arm forming a circular arc and having a central axis;
    means for holding said C-arm and for rotating said C-arm around said central axis;
    a source of acoustic waves which propagate towards said treatment site along an acoustic axis; and
    means for mounting said source of acoustic waves on said C-arm for permitting movement of said source of acoustic waves along said C-arm.

2. An apparatus as claimed in claim 1 wherein said means for holding and rotating said C-arm comprises means for providing said C-arm with a range of rotation through an angle $\beta$ and wherein said means for mounting said source of acoustic waves on said C-arm comprises means for providing said source of acoustic waves with a range of relative movement through an angle $\alpha$ relative to said C-arm, and wherein the sum of $\alpha$ and $\beta$ is at least 360°.

3. An apparatus as claimed in claim 1 further comprising means for rotating said C-arm through at least ±180° around an axis which intersects said central axis of said C-arm.

4. An apparatus for treating a patient with acoustic waves comprising:
    an X-ray locating system including a C-arm partially surrounding a treatment site and an X-ray source and a radiation detector mounted on said C-arm on opposite sides of said treatment site, said C-arm forming a circular arc and having a central axis;
    means for holding said C-arm for rotating said C-arm around said central axis;
    a source of acoustic waves which propagate towards said treatment site along an acoustic axis; and
    means for mounting said source of acoustic waves on said C-arm for permitting circumferental movement of said source of acoustic waves along said C-arm and for maintaining said acoustic axis of said source of acoustic waves in constant intersection with said central axis of said C-arm.

5. An apparatus as claimed in claim 4 wherein said means for holding and rotating said C-arm comprises means for providing said C-arm with a range of rotation through an angle $\beta$ and wherein said means for mounting said source of acoustic waves on said C-arm comprises means for providing said source of acoustic waves with a range of relative movement through an angle $\alpha$ relative to said C-arm, and wherein the sum of $\alpha$ and $\beta$ is at least 360°.

6. An apparatus as claimed in claim 4 wherein said source of acoustic waves is a source of focused acoustic waves which converge in a focus zone lying on said acoustic axis, and wherein said means for maintaining said constant intersection is a means for maintaining said focused zone, at least during treatment with said acoustic waves, on said central axis of said C-arm.

7. An apparatus as claimed in claim 4 further comprising means for rotating said C-arm through at least ±180° around an axis which intersects said central axis of said C-arm.

* * * * *